(12) United States Patent
Flohr et al.

(10) Patent No.: US 6,735,273 B2
(45) Date of Patent: May 11, 2004

(54) X-RAY COMPUTED TOMOGRAPHY APPARATUS AND MULTI-SPECTRA CORRECTION USING A RADIATION PRE-FILTER

(75) Inventors: Thomas Flohr, Uehlfeld (DE); Bernd Ohnesorge, Erlangen (DE)

(73) Assignee: Siemens Aktiengesellschaft, Münich (DE)

( * ) Notice: Subject to any disclaimer, the term of this patent is extended or adjusted under 35 U.S.C. 154(b) by 0 days.

(21) Appl. No.: 10/148,435

(22) PCT Filed: Sep. 27, 2001

(86) PCT No.: PCT/DE01/03717

§ 371 (c)(1),
(2), (4) Date: Oct. 10, 2002

(87) PCT Pub. No.: WO02/26133

PCT Pub. Date: Apr. 4, 2002

(65) Prior Publication Data

US 2003/0053597 A1 Mar. 20, 2003

(30) Foreign Application Priority Data

Sep. 29, 2000 (DE) .......................... 100 48 775

(51) Int. Cl.[7] .......................... G21K 3/00; H05G 1/64
(52) U.S. Cl. .......................... 378/5; 378/98.9; 378/158; 378/159
(58) Field of Search .......................... 378/5, 9, 18, 53, 378/57, 98.9, 124, 134, 136, 137, 156, 157, 158, 159

(56) References Cited

U.S. PATENT DOCUMENTS

| | | | |
|---|---|---|---|
| 3,854,049 A | 12/1974 | Mistretta et al. ............... 378/62 |
| 5,313,510 A | 5/1994 | Ebersberger et al. ......... 378/12 |
| 5,570,403 A | * 10/1996 | Yamazaki et al. .............. 378/5 |
| 5,625,661 A | 4/1997 | Oikawa ........................ 378/15 |
| 5,661,774 A | * 8/1997 | Gordon et al. ............... 378/101 |
| 5,706,326 A | 1/1998 | Gard ........................... 378/19 |
| 6,188,747 B1 | * 2/2001 | Geus et al. .................. 378/124 |
| 6,285,740 B1 | * 9/2001 | Seely et al. ................. 378/98.9 |
| 6,418,189 B1 | * 7/2002 | Schafer ........................ 378/57 |
| 6,597,759 B2 | * 7/2003 | Mazess et al. ................. 378/53 |
| 6,633,627 B2 | * 10/2003 | Horiuchi ...................... 378/156 |
| 6,647,095 B2 | * 11/2003 | Hsieh ........................... 378/159 |

FOREIGN PATENT DOCUMENTS

DE    OS 197 13 400    10/1998

\* cited by examiner

*Primary Examiner*—Edward J. Glick
*Assistant Examiner*—Allen C. Ho
(74) *Attorney, Agent, or Firm*—Schiff Hardin LLP

(57) ABSTRACT

An X-ray computed tomography apparatus has a beam filter arrangement with regions of different filter material or/and different thickness profile of the filter material. This beam filter arrangement is disposed in the beam path preceding an examination subject. For multi-spectra beam hardening correction with estimation of the base material lengths, the computed tomography apparatus is fashioned for implementing projections of the examination subject with different effective material thickness or/and different effective material of the beam filter arrangement.

9 Claims, 2 Drawing Sheets

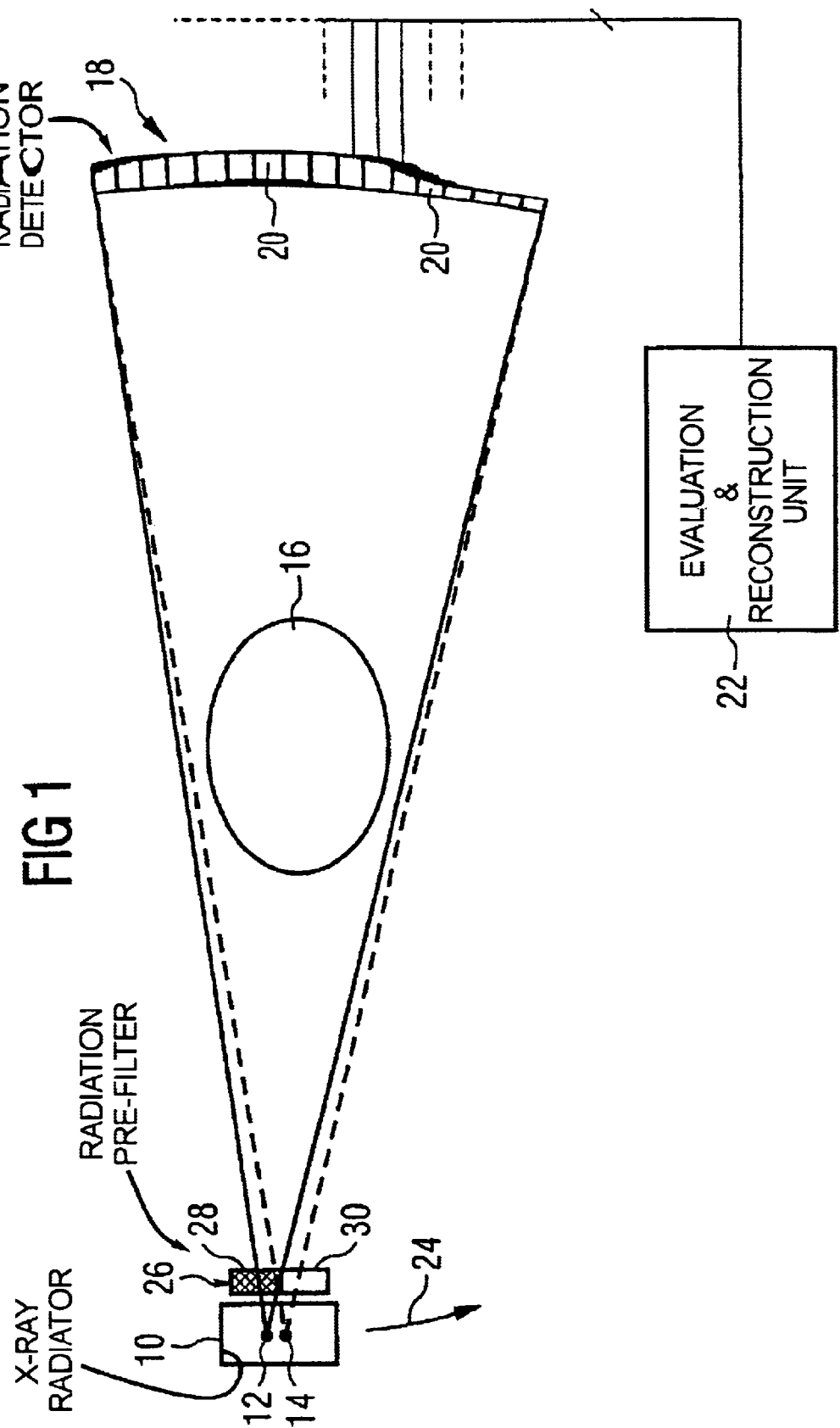

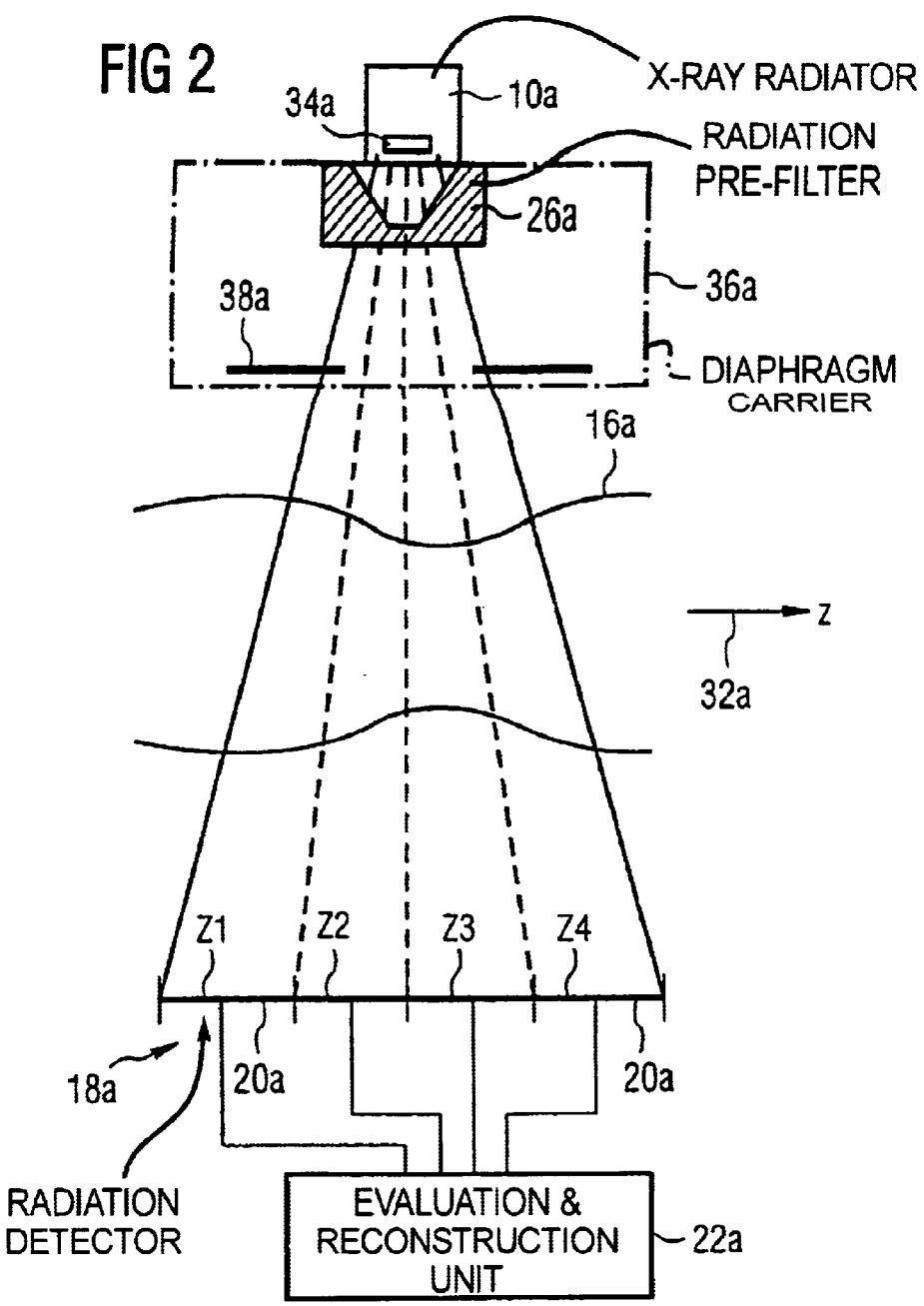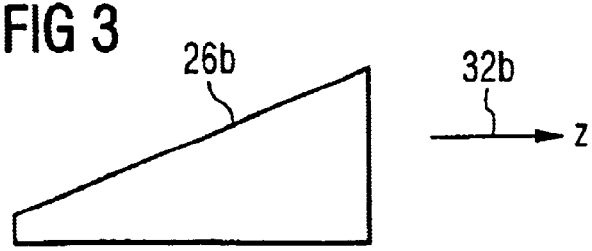

X-RAY COMPUTED TOMOGRAPHY APPARATUS AND MULTI-SPECTRA CORRECTION USING A RADIATION PRE-FILTER

BACKGROUND OF THE INVENTION

1. Field of the Invention

The present invention is directed to an X-ray computed tomography apparatus with multi-spectra beam hardening correction.

2. Description of the Prior Art

The attenuation p that X-radiation generated by an X-ray source experiences in a transirradiated subject is measured in X-ray computed tomography. It is determined from the X-ray intensity I0 incident onto the subject and from the intensity I that is registered in a detector arranged in the beam path following the subject, according to the following equation:

$$p = -1n(I/0) \quad (1).$$

In the case of mono-energetic radiation, the following applies for a homogeneous subject with the attenuation coefficient $\mu$ and the transirradiated subject thickness d:

$$p = \mu d \quad (2).$$

The X-ray attenuation thus increases linearly with the subject thickness.

In fact, however, an X-ray tube emits polychromatic X-radiation with the energy distribution S(E). The attenuation is then calculated according to the following equation:

$$p = \int \cdot \int \mu(E) S(E) dE dx \quad (3).$$

Even when the subject is homogeneous, the X-ray attenuation produced by the subject is thus no longer linearly dependent on the transirradiated subject thickness. Since $\mu E$ usually decreases toward higher energies, the "energy center of gravity" shifts toward higher energies, namely all the more the greater the transirradiated subject thickness is. This effect is referred to as beam hardening.

In image reconstruction methods that are standard in CT technology, a linear change of the X-ray attenuation with the subject thickness is assumed for homogeneous subjects. The overall attenuation p of a beam on its path through a subject composed of partial subjects i with attenuation coefficient $\mu_i$ and thickness $d_i$ then derives from:

$$p = \Sigma_i(\mu_i d_i) \quad (4)$$

The deviations from this assumption caused by the beam hardening lead to data inconsistencies and, thus, to image errors. Typical image errors caused by beam hardening are key artifacts in large, homogeneous subjects and line or bar artifacts in CT images with a high proportion of bone or contrast agent. Current correction methods often have the principal goal or eliminating key artifacts and stripe artifacts in subjects with high attenuation, for instance in shoulder and pelvis exposures. These corrections usually ensue with what is referred to as polynomial correction, whereby a corrected attenuation value $p_c$ is calculated from a detected measured attenuation value $p_M$ by insertion into a polynomial with predetermined coefficients an according to the following equation:

$$p_c = \Sigma_{[n=0.1 \ldots N]}(a_n P_M^n) \quad (5).$$

The coefficients an are acquired, for example, by measuring the attenuation values of uniform absorbers (for example, Plexiglas® bars) given N different thicknesses.

It has been shown that improved correction methods are needed for the correction of locally limited bar and line artifacts as well as unsharp bone-tissue transitions as particularly occur given skull exposures (another known stripe artifact, for example, is what is referred to as the Hounsfield stripe between the petrous bones). An approach has thereby proven beneficial wherein the length of the "base material" that the X-ray beam leading to a measured value has traversed in the body of the patient under examination is individually estimated for each measured attenuation value. In medical examinations, bone substance and soft tissue or, respectively, water, which has spectral attenuation properties similar to soft tissue, are usually selected as base materials. A method referred to as the two-spectra method, for example, is known from the pertinent literature for estimating the base material lengths traversed by an X-ray beam. In this method, two measured values with respectively different spectral energy distribution of the X-ray, which is equivalent to a different average energy of the X-ray, are registered. Given known attenuation coefficients $\mu_W(E_1)$ and $\mu_W(E_2)$ of water at the average spectral energies $E_1$ and $E_2$ and $\mu_K(E_1)$ and $\mu_K(E_2)$ of bone at these average energies, the following, approximate estimate is possible for the measured attenuation values $p(E_1)$ and $p(E_2)$ obtained given there energies $E_1$ and $E_2$:

$$p(E_1) = d_W \cdot \mu_W(E_1) + d_K \cdot \mu_K(E_1) \quad (6a)$$

$$p(E_2) = d_W \cdot \mu_W(E_2) + d_K \cdot \mu_K(E_2) \quad (6b).$$

The water and bone lengths $d_W$ and $d_K$ can then be estimated from these equations.

Corrected measured values $p_c(E_1)$ or, respectively, $p_c(E_2)$ can now be respectively determined in the following way for the average spectral energies $E_1$ and $E_2$:

$$p_c(E_1) = p(E_1) + f_{E1}(d_W, d_K) \quad (7a)$$

$$p_c(E_2) = p(E_2) + f_{E2}(d_W, d_K) \quad (7b)$$

The correction values $f_{E1}$ and $f_{E2}$ are taken from tables that were determined in advance either computationally or empirically for the average spectral energies E1 and E2.

Further information about the above two-spectra method can be found, for example, in the following publications:

1) P. M. Joseph, R. D. Spiftal, Journal of Computer Assisted Tomography, 1978, Vol.2, p.100;
2) P. C. Johns, M. Yaffe, Medical Physics, 1982, Vol.9, p.231;
3) G. H. Glover, Medical Physics, 1982, VOl.9, p.860;
4) A. J. Coleman, M. Sinclair, Physics in Medicine and Biology, 1985, Vol.30, No.11, p.1251.

In order to register measured values at two different average energies in a conventional CT apparatus, two successive revolutions of the X-radiator around the patient must be implemented. In the second revolution, a different beam prefiltering or a different tube voltage is used compared to the first revolution. A disadvantage of such a procedure, however, is that the measured results can exhibit inconsistencies due to patient movement or contrast agent flow.

SUMMARY OF THE INVENTION

It is an object of the present invention to provide a computed tomography apparatus which avoids the aforementioned disadvantages of conventional computed tomography systems.

This object is achieved in accordance with the principles of the present invention in an X-ray computed tomography apparatus having an X-ray radiator with at least two spring foci between which the X-ray radiator is switched to alternatingly emit X-ray beams respectively from the foci, a radiation detector disposed in the X-ray beams, with an examination subject adapted to be disposed between the X-ray radiator and the radiation detector, the radiation detector having a number of detection channels, a beam filter arrangement disposed in said X-ray beams preceding said subject, the beam filter arrangement having regions of different filter characteristics respectively allocated to the foci to give the X-ray beams respectively different energies that the subject, and wherein the X-ray radiator irradiates a slice of the subject with the X-ray beams from a number of projection angles with the X-ray beams, after attenuation by the subject, being incident on detector channels of the radiation detector in a projection range. The radiation detector, for each detector channel in the projection range, generates at least two measured projection values for the respective X-ray beams at different energies from the foci. The measured projection values are supplied to an electronic and evaluation reconstruction unit connected to the radiation detector, which determines a beam hardening-corrected projection value for each of the measured projection values, and reconstructs a tomographic image of the slice of the examination subject using these corrected projection values.

The different regions of the filter arrangement achieve the aforementioned different energy-influencing filter characteristics by being of different filter material, or being of the same filter material but having respectively different thickness profiles in the regions.

The varying material or/and the varying material thickness of the beam filter arrangement make it possible to realize different average energies of the X-rays entering into the examination subject with a single beam filter arrangement without having to change the beam filter arrangement. In particular, the projection measured values for the various average energies can be registered in immediate chronological proximity to one another, so that falsifying influences on the projection measured values due to contrast agent flow and physical movements on the part of the patient area voided. All projection measured values can then be registered in one revolution of the radiator of the radiator-detector arrangement.

Since a multi-spectra correction with estimate of the base material lengths will not be required in all examination scenarios, it is recommended that the beam filter arrangement be interchangeably mounted at the radiator-detector arrangement in order to also keep the employability of the computer tomography apparatus opened for other correction techniques as well.

The beam filter arrangement can be held in a simple way at a diaphragm carrier arranged radiator-proximate that carries a diaphragm arrangement for beam shaping of the x-radiation emitted by the radiator.

The evaluation and reconstruction unit can be fashioned for determining an effective projection value by weighted summation from corrected projection values determined in allocation to respectively one of the detection channels and respectively allocated to one of the spring foci and for reconstructing the tomographic image upon employment of the effective projection values. In this way, the effect can be compensated that the projection measured values of a detection channel are registered at different spectra.

The spring focus mode, however, also allows for the possibility of realizing slice projections of enhanced sampling density by fashioning the evaluation and reconstruction unit for reconstructing the tomographic image for a plurality of projection channels per slice projection that is equal to a multiple of the plurality of detection channels lying within the projection region of the respective slice projection corresponding to the number of spring foci. The evaluation and reconstruction is fashioned for employing the corrected projection values determined in allocation to respectively one of the detection channels for all spring foci in the reconstruction of the tomographic image as corrected projection values of neighboring projection channels.

The inventive also can be advantageously utilized in computed tomography devices wherein the detector of the radiator-detector arrangement is implemented with a number of detector elements arranged in at least two lines lying above one another, an identical detection channel being allocated to their detector elements lying above one another in a respective column. In this case, the beam filter arrangement—in allocation to at least a sub-plurality of at least two detector elements of each column of detector elements lying within the projection region of a slice projection—can respectively comprise a region of different filter material or/and different thickness profile of the filter material. The radiator-detector arrangement is then fashioned for supplying a respective projection measured value for each detector element from this sub-plurality of detector elements in allocation to each column of detector elements lying within the projection region of this slice projection.

In order to avoid subjectively perceived changes between tomographic images based on the employment of different energy spectra that are reconstructed from the projection measured values of successive lines of detector elements, the evaluation and reconstruction unit can be fashioned for determining an effective projection value by weighted summation from the corrected projection values determined in allocation to respectively one of the columns and respectively allocated to one of the detector elements from the decreased number of detector elements and of reconstructing the tomographic image using the effective projection values.

DESCRIPTION OF THE DRAWINGS

FIG. 1 is a schematic illustration of an exemplary embodiment of an inventive CT scanner operating in a spring focus mode.

FIG. 2 is a schematic illustration of an exemplary embodiment of an inventive multi-line CT scanner.

FIG. 3 schematically illustrates an embodiment of a radiation pre-filter for the CT scanners of FIGS. 1 and 2.

DESCRIPTION OF THE PREFERRED EMBODIMENTS

The CT scanner shown in FIG. 1 has an X-ray radiator 10 having two identical foci 12, 14 between which the X-ray radiator 10 can skip back and forth. Proceeding from each of the foci 12, 14, the X-ray radiator 10 can emit X-rays onto the body 16 of a patient under examination fan-like in one plane. A detector arrangement 18 detects the radiation passing through the body 16. The detector arrangement 18 has a number of detector elements 20 arranged next to one another on a circular arc in the direction of the fan angle, each of these detector elements 20 covering a part of the total projection region of the slice projection generated by irradiation of the body 16. Each of the detector elements 20 outputs an intensity measured signal that indicates the intensity of the incident radiation in the respective subregion of the projection, outputting this to an electronic evaluation and reconstruction unit 22. The radiation intensity arriving in each individual sub-region of the projection is thus detected in its own detection channel. Using the incoming intensity measured signals, the evaluation and reconstruction unit 22 respectively determines an attenuation measured value that indicates the beam attenuation in the respective sub-region of the projection.

The radiator 10 is movable around the body 16 in a rotary direction 24 and implements slice projections of the body 16 from a number of projection angles. Two slice projections are taken at each projection angle, one using the focus 12 and one using the focus 14.

In order to be able to implement a two-spectra beam hardening correction of the attenuation measured values obtained given the slice projections, the two slice projections taken at each projection angle are implemented with different average energies of the x-radiation entering into the body 16 under examination. To this end, a beam pre-filter 26 is arranged in the beam path of the x-radiation preceding the body 16, different average spectral energies for the two foci 12, 14 being capable of being set with said radiation pre-filter 26. The radiation pre-filter 26 has two filter regions 28, 30 that—in the illustrated exemplary embodiment—differ as to their filter material given the same material thickness but, alternatively or additionally, can also have a different thickness profile. The radiation pre-filter 26 is arranged such that the filter region 28 is effective given employment of the focus 12, whereas the filter region 30 is effective given employment of the focus 14. The different filter material of the filter regions 28, 30 then produces the desired difference in the average spectral energies. Although this cannot be seen in FIG. 1, the radiation pre-filter 26 is expediently curved such that the path that all individual rays of the ray fan beamed out by the radiator 10 traverse the radiation pre-filter 26 is approximately the same, so that an additional calibration of the detection channels can be avoided.

On the basis of the attenuation measured values acquired at the various average spectral energies, the evaluation and reconstruction unit 22 implements an estimate of the lengths of the base materials traversed by the x-rays in the body 16. Water and bone are considered below as base materials. It is assumed that the base material lengths $d_W(k)$ and $d_K(k)$ of water and bone to be estimated for each individual detection channel k are approximately the same given the two projections that are implemented at each projection angle with the focus 12 and with the focus 14. The following estimate then applies for the attenuation measured values $p_{E1}(k)$ and $p_{E2}(k)$ that the evaluation and reconstruction unit 22 determines for each detection channel k at the two average spectral energies E1 and E2:

$$p(k,E1)=d_W(k)\mu_W(E1)+d_K(k)\mu_K(E1) \quad (8a)$$

$$p(k,E1)=d_W(k)\mu_W(E2)+d_K(k)\mu_K(E1) \quad (8b)$$

The two unknowns $d_W(k)$ and $d_K(k)$ can be determined from this equation system. The evaluation and reconstruction unit 22 then calculates corrected attenuation values $p_c(k, E1)$ and $p_c(k, E2)$ given recourse to previously determined tables, from which it takes correction values $f_{E1}$ and $f_{E2}$ dependent on the values $d_W$ and $d_K$:

$$p_c(k, E1)=p(k, E1)+f_{E1}(d_W(k),d_K(k)) \quad (9a)$$

$$p_c(k, E2)=p(k, E2)+f_{E2}(d_W(k),d_K(k)) \quad (9b)$$

A tomographic image could then be reconstructed merely from the corrected attenuation values $p_c(k, E1)$, and also could be reconstructed only from the attenuation values $p_c(k, E2)$. In both instances, a tomographic image would be reconstructed with a channel number N per slice projection that is equal to the number of detection channels formed by the detector arrangement 18, i.e. equal to the plurality of detector elements 20 lying next to one another in the direction of the fan angle in the respective overall projection region. It might seem that the same tomographic image derives in both instances. In fact, however, it is possible that image differences can be found due to the measured values having been registered with different average spectral energies. In order to compensate this effect, a tomographic image can be reconstructed from data obtained from a weighted summation of the attenuation values $p_c(k, E1)$ and $p_c(k, E2)$. In the case of an averaging with identical weighting, attenuation values $p_c'(k)$ are obtained from the following:

$$p_c'(k)=0.5[p_c(k, E1)+p_c(k, E2)] \quad (10)$$

It is self-evident that a different weighting of the attenuation values $p_c(k, E1)$ and $p_c(k, E2)$ can also be undertaken whenever desired.

Alternatively, it is conceivable that a tomographic image be reconstructed with an increased channel number M by considering the corrected attenuation values $p_c(k, E1)$ and $p_c(k, E2)$ as being the result of a single projection. Attenuation values $p_c''(1)$ are thereby formed in the following way by interleaving the attenuation values $p_c(k, E1)$ and $p_c(k, E2)$:

$$p_c''(1=2k)=p_c(k, E1) \quad (11a)$$

$$p_c''(1=2k-1)=p_c(k, E2) \quad (11b)$$

wherein k=1, 2, . . . N. In this way, an attenuation value $p_c''(1)$ is obtained for each channel 1 from a number M of projection channels that is twice as great as the number N of the detection channels formed by the detector arrangement 18.

The further discussion is based on FIGS. 2 and 3. Identical components or components having the same effect as in FIG. 1 are thereby provided with the same reference characters but supplemented by a lower case letter. In order to avoid repetitions, essentially only the differences compared to the exemplary embodiment of FIG. 1 shall be explained. For the remainder, the above description of FIG. 1 applies.

The CT scanner shown in FIG. 2 is a type referred to as a multi-line scanner that has detector elements 20a in a number of lines lying above one another in the direction of a z-axis 32a. The z-axis 32a corresponds to the feed axis along which the patient 16a is moved through CT scanner. In the illustrated exemplary embodiment of FIG. 2, the detector arrangement 18a has four such lines of detector elements 20a; the lines are referenced Z1, Z2, Z3 and Z4. The X-ray radiator 10a is fashioned for implementing a slice projection of the body 16a at each projection angle for each detector line. In the exemplary case, thus, four slice projections following one another in the direction of the Z-axis can be registered at each projection angle. All detector elements 20a lying above one another in a column supply measured signals at these four slice projections that given a view in the direction of the fan angle of the radiation band emitted by the radiator 10a from a focus 34a at each slice projection—can be respectively allocated to the same detection channel. In order to implement a multi-spectra attenuation measurement given the multi-line scanner of FIG. 2, the radiation pre-filter 26a that is attached focus-proximate has regions of different thickness profile or/and different filter material in the direction of the z-axis. Dependent on the design of the radiation pre-filter 26a, a different average spectral energy of the X-rays can be obtained for each detector line, or the same average spectral energy can be obtained for each of groups of detector lines. In the exemplary case of FIG. 2, the radiation pre-filter 26a has a thickness that varies in the z-direction. The radiation pre-filter 26 is symmetrically designed in z-direction such that the same filter effect is achieved for each of the inner detector lines Z2 and Z3.

Because the radiation pre-filter 26a extends over all detector lines in the z-direction and no discontinuous transitions of the filter effect occur, the artifacts susceptibility of the tomographic images reconstructed for the individual detector lines is decidedly slight even given imprecise adjustment or mechanical movement of the pre-filter or given unavoidable gravitational or thermal z-movement of the focus 34a during the revolution of the radiator 10a around the patient 16a. A steady curve of the filter effect of the radiation pre-filter 26a is therefore preferred in z-direction.

The radiation pre-filter 26a can be mounted in a diaphragm box 36a (indicated with broken lines) wherein a diaphragm arrangement 38a is accommodated that serves the purpose of beam shaping of the x-radiation emitted by the radiator 10a in z-direction and in the direction of the fan angle. Together with a conventional, auxiliary pre-filter arrangement (not shown in detail), the radiation pre-filter 26a can thereby releasably mounted on a common changing device, so that it is removable as needed and can only be brought into use for specific purposes (for example, exposures of the base of the skull).

The following description of a multi-spectra beam hardening correction for the CT scanner shown in FIG. 2 having four detector lines Z1 through Z4 can be transferred without difficulty to other CT scanners having a different number of lines. A two-spectra correction shall be considered first for the case of the radiation pre-filter 26a according to FIG. 2 that is symmetrical relative to the middle of the detector. For the line pair Z1 and Z2, the different effective thickness of the radiation pre-filter 26a supplies spectra having different average quantum energy $E_1$ or, respectively, $E_2$. The same is true for the line pair Z3 and Z4. Given the assumption of approximately identical estimated values for $d_W$ and $d_K$ for both detector lines of the respective line pair, a corrected attenuation value can be respectively calculated. The following then applies for the channels k of a projection $p_i(k, Ej)$, registered at the effective energy Ej (j=1,2) in the detector line i (i=1,2,3,4):

$$p_1(k, E1) = d_{W1}(k)\mu_W(E1) + d_{K1}(k)\mu_K(E1) \quad (12a)$$

$$p_2(k, E2) = d_{W1}(k)\mu_W(E2) + d_{K1}(k)\mu_K(E2) \quad (12b)$$

$$p_3(k, E2) = d_{W2}(k)\mu_W(E2) + d_{K2}(k)\mu_K(E2) \quad (12c)$$

$$p_4(k, E1) = d_{W2}(k)\mu_W(E1) + d_{K2}(k)\mu_K(E1) \quad (12d)$$

Using the Equations (12a) through (12d), the base material lengths $d_{W1}$ and $d_{W2}$ can now be determined for water (soft tissue) as well as $d_{K1}$ and $d_{K2}$ for bone. Employing correction factors $f_{Ej}(d_{Wv}(k), d_{Kv}(k))$ (v=1,2) that, for example, are taken from pre-calculated tables, corrected attenuation values $p_{ci}(,Ej)$ for all detector lines i (i=1,2,3,4) can then be determined in the following way:

$$p_{c1}(k, E1) = p_1(k, E1) + f_{E1}(d_{W1}(k), d_{K1}(k)) \quad (13a)$$

$$p_{c2}(k, E2) = p_2(k, E2) + f_{E2}(d_{W1}(k), d_{K1}(k)) \quad (13b)$$

$$p_{c3}(k, E2) = p_3(k, E2) + f_{E2}(d_{W2}(k), d_{K2}(k)) \quad (13c)$$

$$p_{c4}(k, E1) = p_4(k, E1) + f_{E1}(d_{W2}(k), d_{K2}(k)) \quad (13d)$$

When an individual tomographic image for each of the different detector lines is reconstructed from the corrected attenuation values $p_{ci}(k,Ej)$, it may occur that the image impression subjectively changes between the lines of the line pair Z1 and Z2 and between the lines of line pair Z3 and Z4 due to the respectively different average spectral energy. In order to avoid this effect, the separately corrected attenuation values $p_{ci}(k, Ej)$ of the different detector lines can be averaged to form attenuation values $P_{cq}(k,E_{eff})$ of two effective detector lines q (q=1,2):

$$p_{c1}(k, E_{eff}) = 0.5[p_{c1}(k, E1) + p_{c2}(k, E2)] \quad (14a)$$

$$p_{c2}(k, E_{eff}) = 0.5[p_{c3}(k, E2) + p_{c4}(k, E1)] \quad (14b)$$

A common tomographic image is reconstructed for the detector lines Z1 and Z2 from the effective attenuation values $p_{c1}(k,E_{eff})$, whereas a common tomographic image for the detector lines Z3 and Z4 is reconstructed from the effective attenuation values $p_{c2}(k, E_{eff})$. The same effective energy $E_{eff}$ is allocated to the effective attenuation values $p_{c1}(k,E_{eff})$ and $p_{c2}(k,E_{eff})$.

The projections also can be combined with different weighting of the individual attenuation values $p_{ci}(k,Ej)$ in order to intensify the image effectiveness of one of the two energies $E_1$ and $E_2$:

$$p_{c1}(k, E_{eff}) = g_1 p_{c1}(k, E1) + g_2 p_{c2}(k, E2) \quad (15a)$$

$$p_{c2}(k, E_{eff}) = g_2 p_{c3}(k, E2) + g_1 p_{c4}(k, E1) \quad (15b)$$

wherein $g_1 + g_2 = 1$.

Moreover, a utilization of the four detector lines Z1 through Z4 at four different energy spectra is conceivable, even though the outlay then rises in view of calculating time and table generation. In such a four-spectra correction, further base materials could be taken into consideration, for example iodine-containing water solutions. Beam hardening errors that occur given exposures of the brain and other body parts as a consequence of the employment of iodine-containing contrast agent could then be eliminated. FIG. 3 shows a possible structure of a radiation pre-filter 26b in order to realize a four-spectra mode of the four-line scanner of FIG. 2. The radiation pre-filter 26b fabricated, for example, of titanium exhibits a thickness that changes uniformly in the z-direction 32b over all detector lines.

Given four detector lines under consideration, the following equation system derives for determining the base material lengths $d_W$ of water, $d_K$ of bone and $d_X$ and $d_Y$ of two further materials X and Y. It must be assumed that the four base material lengths $d_W$, $d_K$, $d_X$, $d_Y$ to be determined are at least approximately constant for all detector lines under consideration.

$$p_1(k, E1) = d_w(k)\mu_W(E1) + d_K(k)\mu_K(E1) + d_X(k)\mu_X(E1) + d_Y(k)\mu_Y(E1) \quad (16a)$$

$$p_2(k, E2) = d_w(k)\mu_W(E2) + d_K(k)\mu_K(E2) + d_X(k)\mu_X(E2) + d_Y(k)\mu_Y(E2) \quad (16b)$$

$$p_3(k, E3) = d_w(k)\mu_W(E3) + d_K(k)\mu_K(E3) + d_X(k)\mu_X(E3) + d_Y(k)\mu_Y(E3) \quad (16c)$$

$$p_4(k, E4) = d_w(k)\mu_W(E4) + d_K(k)\mu_K(E4) + d_X(k)\mu_X(E4) + d_Y(k)\mu_Y(E4) \quad (16d)$$

When the four base material lengths have been determined on the basis of this equation system, a correction factor $f_{Ev}(d_W(k), d_K(k), d_X(k), d_Y(k))$ can be taken from previously determined tables for all energies $E_v$(v=1,2,3,4). The corrected attenuation values $p_{cv}(k,E_v)$ are then calculated in a manner analogous to the two-spectra method:

$$p_{cv}(k, Ev) = pv(k, Ev) + f_{Ev}(d_W(k), d_K(k), d_X(k), d_Y(k)) \quad (17)$$

wherein ν=1,2,3,4. In this case as well, an image reconstruction can individually cause a subjectively buried image impression from line to line for each of the detector lines. By weighted combination of all four corrected projections, this can again be avoided:

$$p_c(k,E_{eff}) = \Sigma_{[v=1,2,3,4]}[g_v p_{cv}(k,Ev)] \qquad (18)$$

wherein $\Sigma_{[v=1,2,3,4]}$ gv=1. A common tomographic image from these effective attenuation values is then reconstructed for all four detector lines.

It must be added that the invention, of course, also can be employed with multi-line scanners having spring focus mode, and it is then possible to employ a radiation pre-filter that has thickness variations or/and material variations in the direction of the fan angle as well as in the z-direction.

Although modifications and changes may be suggested by those skilled in the art, it is the invention of the inventors to embody within the patent warranted heron all changes and modifications as reasonably and properly come within the scope of their contribution to the art.

What is claimed is:

1. An X-ray computed tomography apparatus comprising:
   an X-ray radiator having at least two spring foci between which said X-ray radiator is switched to alternatingly emit X-ray beams respectively from said foci;
   a radiation detector disposed in said X-ray beams, with an examination subject adapted to be disposed between said X-ray radiator and said radiation detector, said radiation detector comprising a plurality of detector channels;
   a beam filter arrangement disposed in said X-ray beams preceding said subject, said beam filter arrangement having regions of different energy-influencing filter characteristics respectively allocated to said foci to give said X-ray beams respectively different energies at said patient;
   said X-ray radiator irradiating a slice of said subject with said X-ray beams from a plurality of projection angles, said X-ray beams, after attenuation by said subject, being incident on detector channels of said radiation detector in a projection range, and said radiation detector, for each detector channel in said projection range, generating at least two measuring projection values for the respective X-ray beams at different energies from said foci; and
   an electronic evaluation and reconstruction unit connected to said radiation detector and supplied with said measured projection values, for determining a beam hardening-corrected projection value for each of the measured projection values, and for reconstructing a tomographic image of said slice of said subject using said beam hardening-correct projection values.

2. An X-ray computed tomography apparatus as claimed in claim 1 wherein said beam filter arrangement has regions of different energy-influencing material.

3. An X-ray computed tomography apparatus as claimed in claim 1 wherein said beam filter arrangement has regions of respectively different energy-influencing thickness profiles.

4. An X-ray computed tomography apparatus as claimed in claim 1 wherein said beam filter arrangement is interchangeably mounted between said X-ray radiator and said radiation detector.

5. An X-ray computed tomography apparatus as claimed in claim 1 comprising a diaphragm carrier mounted at a location proximate said X-ray radiator, said diaphragm carrier carrying a diaphragm arrangement for shaping said X-ray beams emitted from said foci, and wherein said beam filter arrangement is mounted at said diaphragm carrier.

6. An X-ray computed tomography apparatus as claimed in claim 1 wherein said evaluation and reconstruction unit determines, for each of said detection channels, and effective projection value by a weighted summation of the beam hardening-corrected projection values for that detection channel, and reconstructs said tomographic image using the respective effective projection values for said detection channels in said projection range.

7. An X-ray computed tomography apparatus as claimed in claim 1 wherein said evaluation and reconstruction unit reconstructs said tomographic image using beam hardening-corrected projection values from a plurality of detection channels equal to a multiple of a plurality of detection channels within said projection region corresponding to a plurality of said spring foci, and said evaluation and reconstruction unit employing the beam hardening-corrected projection values for each of said detection channels for each of said spring foci for reconstructing said tomographic image among neighboring detection channels.

8. An X-ray computed tomography apparatus as claimed in claim 1 wherein said radiation detector comprises a plurality of detector lines, each detector line comprising a plurality of detector elements with said detector elements being disposed in columns proceeding substantially perpendicularly to said lines, with the detector elements in the respective columns forming said detector channels and wherein said regions of said beam filter arrangement are respectively allocated to at least two detector elements of each column within said projection region, and wherein said radiation detector supplies said measured projection values from the respective columns of detector elements.

9. An X-ray computed tomography apparatus as claimed in claim 8 wherein said evaluation and reconstruction unit determines, for each of said columns, an effective projection value by a weighted summation of the beam hardening-corrected projection values from the respective detector elements in that column, and reconstructs said tomographic image of said slice using said effective projection values from the respective columns.

* * * * *